United States Patent [19]

Trecker

[11] 4,034,770
[45] July 12, 1977

[54] DENTAL FLOSS WITH FINGER LOOPS

[76] Inventor: Francis J. Trecker, 7100 Mummy Mountain Road, Scottsdale, Ariz. 85253

[21] Appl. No.: 654,215

[22] Filed: Feb. 2, 1976

[51] Int. Cl.² .......................................... A61C 15/00
[52] U.S. Cl. ................................................. 132/90
[58] Field of Search ................ 132/90, 91, 92, 79 E

[56] References Cited

U.S. PATENT DOCUMENTS

| 1,287,926 | 12/1918 | Ecaubert | 132/92 A |
|---|---|---|---|
| 1,488,810 | 4/1924 | Fraser | 132/79 E |
| 2,162,240 | 6/1939 | Boldusoff | 132/91 |
| 2,648,341 | 8/1953 | Moll | 132/91 |
| 3,744,499 | 7/1973 | Wells | 132/92 A |
| 3,802,445 | 4/1974 | Wesley | 132/89 |

Primary Examiner—G.E. McNeill
Attorney, Agent, or Firm—Cyril M. Hajewski

[57] ABSTRACT

Conventional dental floss is provided with loops at convenient intervals along its length. The person using the dental floss can insert a finger from each hand into two adjacent loops to obtain a firm grip on the dental floss while it is being used to remove particles from between the teeth. The dental floss with the loops on it is rolled into a coil in the usual manner and placed in a container from which it can be drawn for use.

2 Claims, 4 Drawing Figures

DENTAL FLOSS WITH FINGER LOOPS

BACKGROUND OF THE INVENTION

Dental floss is a well known product that has been employed for removing particles of food or the like from between a person's teeth. It is a thread, except that in order to be effective it must be smooth and glossy to permit it to slip easily between the teeth. The thread used for this purpose is usually made of silk fibers to form a soft lustrous material and is then waxed so that it will be especially effective for cleaning between the teeth. As a result, the dental floss is very slippery and difficult to grip.

It is the general practice for a person to draw a long length of dental floss and wind it about his fingers in order to obtain a grip on it. This results in a great deal of waste. In order to avoid such waste various appliances have been devised for gripping and stretching a length of dental floss between two arms or the like and using such stretch of dental floss to clean the teeth. Such appliances are relatively large, but the main objection to them is that they are exposed to dirt and contamination when not in use and a part of the appliance must be placed in the mouth when using it. It is distasteful to most people to place such item in their mouths and it may be harmful.

It is therefore a general object of the present invention to provide an improved dental floss with built in grips that are sanitary but very effective for gripping the dental floss when placing it in use.

It is a further object of the present invention to provide grips on dental floss that may be gripped by the user of the dental floss with such grips being formed by the dental floss itself and wound in the coil with the dental floss so that they are maintained in a sanitary condition.

SUMMARY OF THE INVENTION

According to this invention the improved dental floss comprises the conventional material used for this purpose with spaced loops along the length of the dental floss formed by tying the dental floss. The loops are large enough to permit a finger of the human hand to be inserted into the loop for firmly gripping the dental floss when it is put to use. They are spaced apart a sufficient distance to establish a useable length of dental floss between them. Cutoff sections are disposed between the useable lengths of dental floss to provide a relatively short length of dental floss where the useable length with two loops attached may be separated from the continuous length of dental floss.

The dental floss with the loops attached is wound onto a reel that is placed in a dispensing container. The dental floss is unwound from the reel and extracted from the dispenser for use. The loops will be attached to the dental floss as it leaves the dispenser and a cutter is available on the dispenser for severing the dental floss at a cutoff section so that the user has one useable length of dental floss with two spaced finger loops on it for cleaning his teeth.

DESCRIPTION OF THE PREFERRED EMBODIMENT

Figure 1:
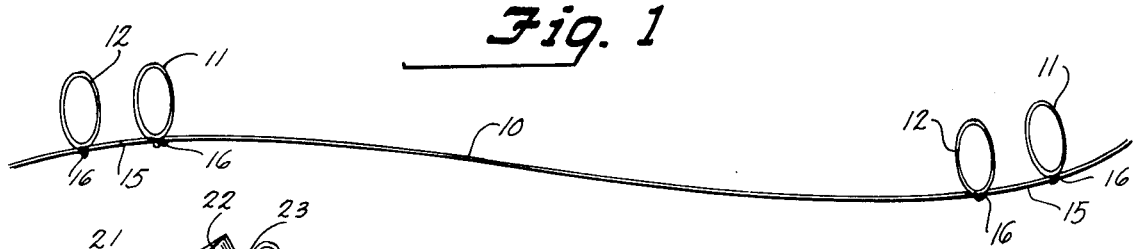
FIG. 1 is a perspective view of a length of dental floss having finger loops attached to it in accordance with the teachings of the present invention.
Figure 2:
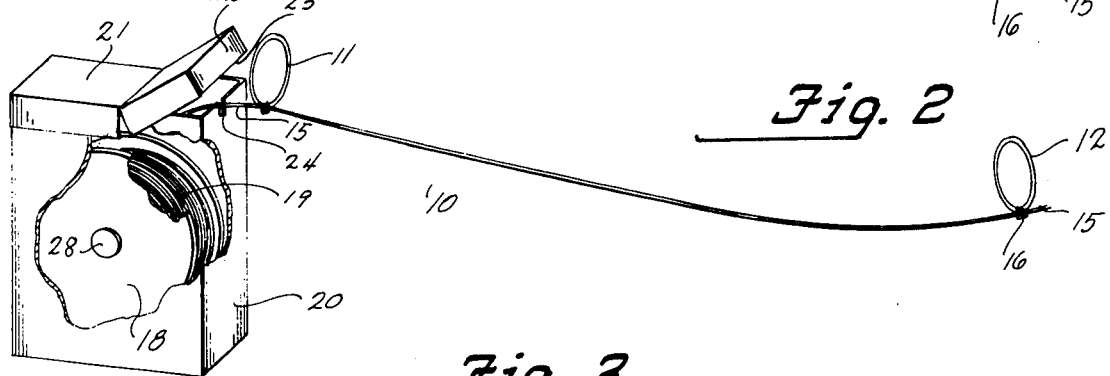
FIG. 2 is a perspective view of a dental floss container with its cover open and a length of dental floss constructed in accordance with the teachings of the present invention extending out of the container.

Reference is now made more particularly to the drawing and specifically to FIG. 1 thereof which illustrates a useable length of dental floss 10 disposed between two finger loops 11 and 12.

In addition to the useable lengths 10 the dental floss includes cutoff sections 15 which are of much shorter lengths than the useable lengths 10 and are included in the supply of dental floss for the purpose of providing a length where the useable length 10 and its two finger loops 11 and 12 may be separated from the rest of the continuous length of dental floss. The cutoff sections 15 are also disposed between two finger loops 11 and 12 as clearly shown in FIG. 1 but are not of sufficient length to conveniently use for cleaning the teeth.

The finger loops 11 and 12 may be separate lengths of material secured to the dental floss but are preferably all formed of the same length of dental floss by merely tying a knot 16 in the dental floss with a loop extending from the straight length of dental floss.

Figure 4:
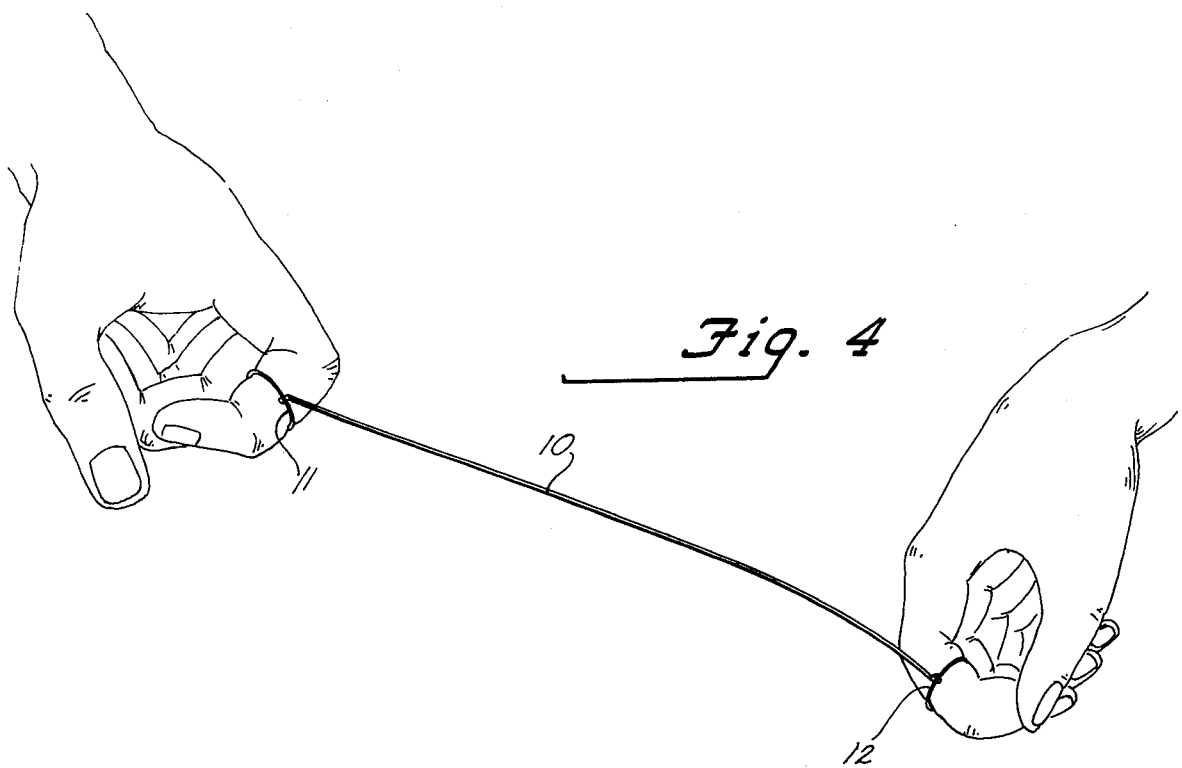
FIG. 4 is a perspective view of a useable length of dental floss being held by human hands with a finger of each hand being inserted in one finger loop for gripping the dental floss.

Dental floss is a thread usually manufactured from silk fibers to form a soft lustrous material which is waxed to make it especially effective for cleaning particles of food or the like from between the teeth of a human being. As a result, the dental floss is very slippery and since it is just a thread it is difficult to hold when using it to clean the teeth. The finger loops 11 and 12 serve as excellent grips for gripping a length of dental floss when using it to clean the teeth. To this end, as clearly shown in FIG. 4, the user will place a finger of one hand within the finger loop 11 and a finger of the other hand within the finger loop 12. With two fingers of two hands thus in the loops 11 and 12 the user has a firm grip on the dental floss and the useable length 10 of dental floss may then be employed with facility for cleaning the teeth.

In order that a useable length 10 with two finger loops 11 and 12 attached to it may be always separated from the continuous length of dental floss, the cutoff sections 15 are provided between each useable length 10 and these cutoff sections 15 are of relatively short length where the cut will take place to separate the preceding useable length 10 from the continuous length of dental floss.

The useable lengths 10 with the cutoff sections 15 and finger loops 11 and 12 are all wound together on a reel 18 to form a coil 19 which is a continuous length of dental floss that is stored in a container 20. The container 20 includes a stationary lid 21 and a hinged cover 22 which includes a knife edge 23.

Figure 3:
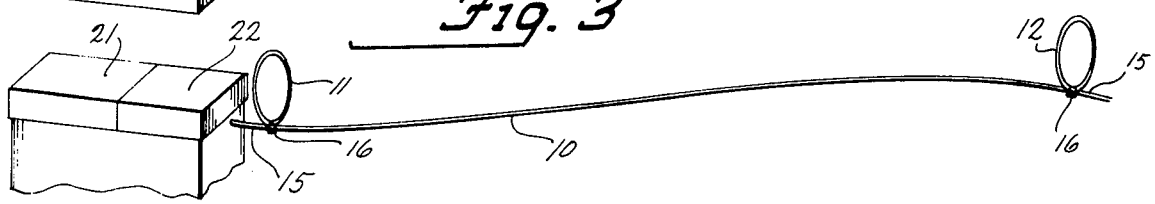
FIG. 3 is a perspective view of the container and dental floss shown in FIG. 2 with its cover closed for cutting the dental floss to separate the length that is extending out of the container from the coil of dental floss in the container.

The container 20 has a notch 24 through which the dental floss 10 passes as it emerges from the container 20. When the cutoff section 15 arrives at the notch 24 it is only necessary to close the hinged cover 22 to the position shown in FIG. 3 to sever the dental floss at the cutoff section 15 to thereby separate the preceding useable length 10 and its finger loops 11 and 12 from the continuous length of dental floss in the container 20.

As previously mentioned, the continuous length of dental floss in the container 20 is wound on the reel 20 to form the coil 19. The reel 20 is rotatably supported in the container 20 on a pin 28 so that it will readily permit withdrawal of the dental floss from the container 20 by unwinding it from the coil 19 on the reel 18.

From the foregoing detailed description of the illustrative embodiment of the invention set forth herein it will be apparent that there has been provided an improved arrangement of dental floss which is especially adapted to be gripped by the user by virtue of providing finger loops between useable lengths of dental floss so that the user may insert a finger of each hand into a finger loop to securely hold the useable length of dental floss between the two finger loops.

Although the illustrative embodiment of the invention has been described in considerable detail for the purpose of disclosing a practical, operative arrangement by means of which the invention may be practised advantageously, it is to be understood that the particular dental floss with finger loops illustrated and described is intended to be illustrative only and that the various novel characteristics of the invention may be incorporated in other structural forms without departing from the spirit and scope of the invention as defined in the subjoined claims.

The principles of this invention having now been fully explained in connection with the foregoing description, I hereby claim as my invention:

1. In a device for cleaning the teeth of a human being; a continuous length of thread adapted to be inserted between the teeth and drawn longitudinally for removing particles of food and the like from between the teeth; a plurality of finger loops disposed at intervals along said length of thread to define useable lengths of thread for cleaning teeth between them, such loops being formed by looping the dental thread itself so that the user may insert a finger of each hand into the two loops for gripping the thread while drawing it back and forth between the teeth in a cleaning operation; a knot in the thread at each of said finger loops to secure the loop; a cutoff length of dental thread between each of said useable lengths to provide a length of thread that may be severed for separating the useable lengths of thread from the continuous length of thread without interrupting the useable lengths of thread; and the continuous length of thread with said finger loops attached is wound into a coil from which it may be withdrawn and the useable lengths of thread each with two finger loops attached may be individually separated from the continuous thread by severing the continuous thread at said cutoff lengths.

2. A teeth cleaning device according to claim 1 including; a container for containing said continuous length of thread in a sanitary condition; a reel rotatably supported in said container so that said continuous length of thread can be wound on said reel to form said coil and may be unwound from said reel to withdraw the dental thread from said container; and a knife on said container in position to engage said dental thread at a cutoff length to sever it and thereby separate a useable length of dental thread with its two cooperating finger loops from the continuous thread on said reel.

* * * * *